Figure 1:
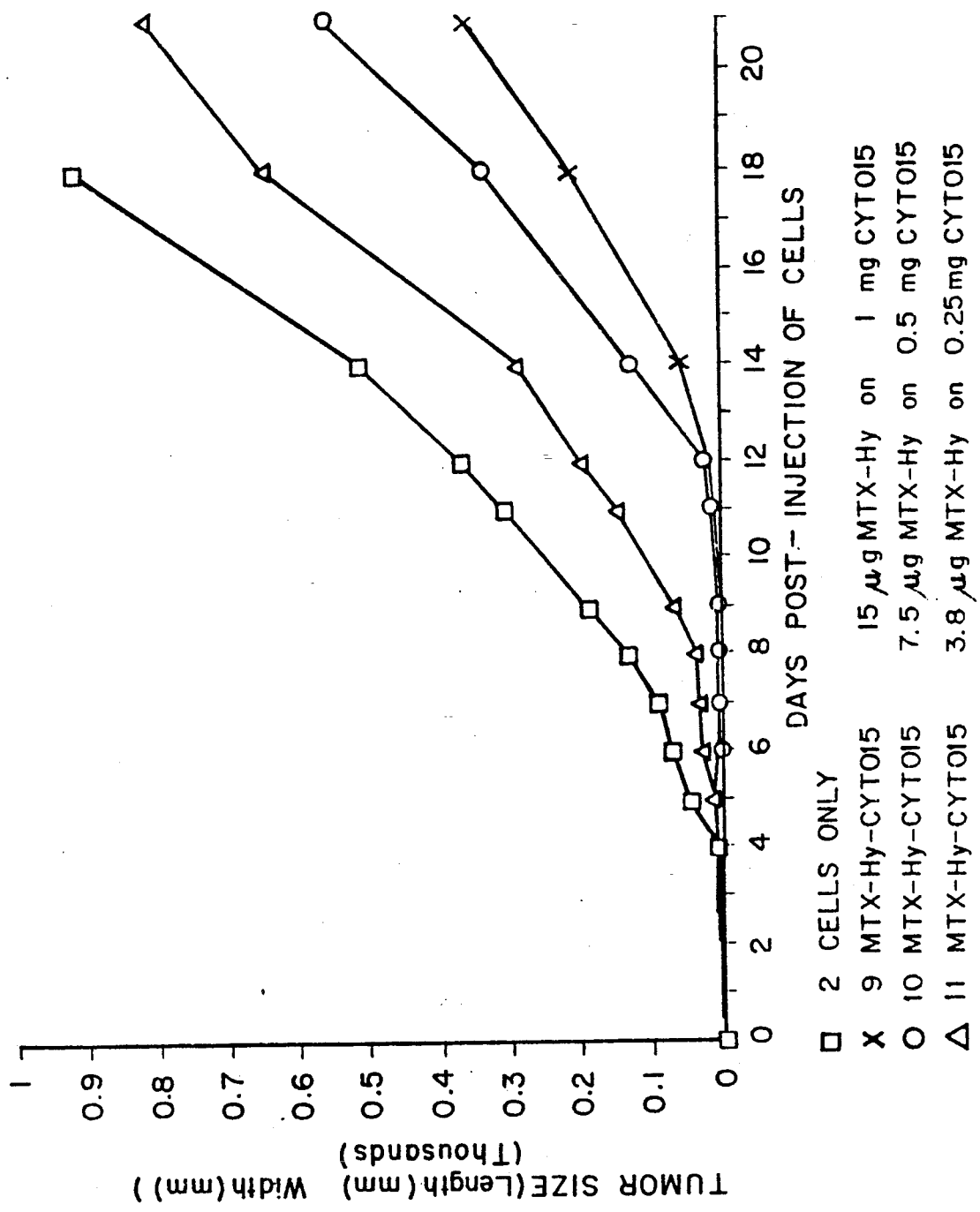

United States Patent [19]

Coughlin et al.

[11] Patent Number: 5,140,104
[45] Date of Patent: Aug. 18, 1992

[54] AMINE DERIVATIVES OF FOLIC ACID ANALOGS

[75] Inventors: Daniel J. Coughlin, Robbinsville, N.J.; John D. Rodwell, Yardley, Pa.

[73] Assignee: Cytogen Corporation, N.J.

[21] Appl. No.: 426,374

[22] Filed: Oct. 24, 1989

Related U.S. Application Data

[63] Continuation of Ser. No. 861,037, May 8, 1986, abandoned, which is a continuation-in-part of Ser. No. 650,375, Sep. 13, 1984, Pat. No. 4,867,973, Ser. No. 650,754, Sep. 13, 1984, abandoned, Ser. No. 646,327, Aug. 31, 1984, abandoned, Ser. No. 646,328, Aug. 31, 1984, Pat. No. 4,741,900, and Ser. No. 356,315, Mar. 9, 1982, Pat. No. 4,671,958.

[51] Int. Cl.$^5$ ............................................. C07D 475/00
[52] U.S. Cl. ..................................... 530/330; 544/260
[58] Field of Search ............... 514/249, 565, 581, 590; 530/387, 388, 389, 391, 330; 544/260

[56] References Cited

U.S. PATENT DOCUMENTS

| | | | |
|---|---|---|---|
| 3,970,521 | 7/1976 | Zaborsky et al. | 195/63 |
| 4,077,957 | 3/1978 | Peper et al. | 544/260 |
| 4,093,607 | 6/1978 | Sela et al. | 260/112 B |
| 4,167,449 | 9/1979 | Gargiulo et al. | 435/16 |
| 4,217,338 | 8/1980 | Quash | 424/1 |
| 4,256,833 | 3/1981 | Ali et al. | 435/7 |
| 4,263,279 | 4/1981 | Sela et al. | 424/85 |
| 4,287,345 | 9/1981 | Kotani et al. | 546/261 |
| 4,314,988 | 2/1982 | Farina et al. | 436/505 |
| 4,393,064 | 7/1983 | DeGraw, Jr. et al. | 514/249 |
| 4,419,444 | 12/1983 | Quash | 435/7 |
| 4,431,805 | 2/1984 | Temple et al. | 544/279 |
| 4,433,147 | 2/1984 | DeGraw, Jr. et al. | 544/260 |
| 4,460,591 | 7/1984 | DeGraw et al. | 514/258 |
| 4,490,529 | 12/1984 | Rosowsky | 544/260 |
| 4,526,964 | 7/1985 | Temple et al. | 544/279 |
| 4,536,575 | 8/1985 | Temple et al. | 544/279 |
| 4,584,375 | 4/1986 | Coward | 544/258 |
| 4,671,958 | 6/1987 | Rodwell et al. | 424/85.91 |

FOREIGN PATENT DOCUMENTS

| | | |
|---|---|---|
| 8117198.4 | 3/1982 | European Pat. Off. . |
| 81107197.6 | 3/1982 | European Pat. Off. . |
| 088695 | 9/1983 | European Pat. Off. . |
| 84305510.4 | 4/1985 | European Pat. Off. . |
| 8540177.6 | 3/1986 | European Pat. Off. . |
| 154520 | 12/1977 | Japan . |
| 155094 | 12/1979 | Japan . |
| 1446536 | 2/1975 | United Kingdom . |
| 2015530 | 9/1979 | United Kingdom . |
| US83/02065 | 7/1985 | World Int. Prop. O. . |

OTHER PUBLICATIONS

Chemical Abstracts, (No.: 33729n), 1989.
Rosowsky et al., *J. Med. Chem.*, 23: (5), pp. 660–667 (1985).
Rosowsky et al., *J. Med. Chem.*, 24: (5), pp. 559–567 (1981).
Rosowsky et al., *J. Med. Chem.*, 24: (12), pp. 1450–1455 (1981).
Burnstein et al., *J. Med. Chem.*, 20: (7), pp. 950–956 (1977).
Uadia et al., *Cancer Research*, 44: pp. 4263–4266 (1984).
Kulkarni et al., *Cancer Research*, 41: pp. 2700–2706 (1981).

(List continued on next page.)

Primary Examiner—Frederick E. Waddell
Assistant Examiner—K. Weddington
Attorney, Agent, or Firm—Pennie & Edmonds

[57] ABSTRACT

Novel therapeutic antibody conjugates comprising amine derivatives of folic acid analogs covalently attached via a reactive amine group to an oxidized carbohydrate moiety of an antibody or antibody fragment are disclosed. The conjugates retain substantially the same immunospecificity and immunoreactivity of the unconjugated antibody molecule. The immunospecificity and immunoreactivity of the antibody conjugates permits targeted delivery of the attached therapeutically effective amine derivative of folic acid analogs in vivo. The conjugates are therapeutically effective against a variety of neoplastic and non-neoplastic cellular disorders when administered in vivo. Methods for synthesizing the amine derivatives of folic acid analogs, methods for preparing the antibody conjugates, and methods for use of the conjugates in vivo are also disclosed.

10 Claims, 2 Drawing Sheets

OTHER PUBLICATIONS

Piper et al., J. Med. Chem., 25: (2), pp. 182–187 (1982).
Anderson and Parrish, Science, 220:524–527 (1983).
Bale et al., Cancer Research, 40:2965–2972 (1980).
Bing, Biochemistry, 8:4503–4510 (1969).
Blythman et al., Nature, 290: 145–146 (1981).
Bunton, in Oxidation in Organic Chemistry, vol. I, Widberg, ed., Academic Press, New York, p. 365 (1965).
Caporale et al., J. Immunol., 126:1963–1965 (1981).
Cooper, Biochemistry, 14:4245–4251 (1975).
Cooper et al., J. Biol. Chem., 234:445–448 (1959).
Davis and Preston, Science, 213:1358–1388 (1981).
Dougherty et al., in Porphyrin Photosensitization, Kessel and Dougherty eds., Plenum Publishing Corp., N.Y., pp. 3–13 (1983).
Ghose et al., J. Natl. Cancer Inst., 61(3):657–676 (1978).
Gregoriadis, Pharmac. Ther., 10:103–118 (1980).
Gregoriadis, Nature, 265:407–411 (1977).
Heath et al., Biochim Biophys. Acta., 640:66–81 (1981).
Huang et al., J. Biol. Chem., 255(17):8015–8018 (1980).
Hurwitz et al., Int. J. Cancer, 24:461–470 (1979).
Jackson, "Periodic Acid Oxidations" in Organic Reactions, vol., pp. 341–375 (1944).
Jentoff and Dearborn, J. Biol. Chem., 254:4359–4365 (1979).
Lesserman et al., Nature, 288:602–604 (1980).
March, in Advanced Organic Chemistry: Reactions; Mechanisms and Structures, McGraw Hill Co., N.Y., pp. 824–825 (1978).
Martin et al., Biochem., 20:4229–4238 (1981).
Mew et al., J. Immunol., 130:1473–1477 (1983).
Mitra and Lawton, J. Amer. Chem. Soc., 101:3097–3110 (1979).
Murayama et al., Immunochem., 15:523–528 (1978).
Parrish, J. Investig. Dermatol., 77:45–50 (1981).
Reid and Porter, Ann. Rev. Biochem., 50:433–464 (1981).
Rowland, in Targeted Drugs, Goldberg ed., Interscience Publications, N.Y., pp. 57–72 (1983).
Sims et al., Biochem. J., 163:219–227 (1977).
Stanworth and Turner, in Handbook of Experimental Immunology, vol. I, 2d ed. Weir, ed. Blackwell Scientific Publications, London, Chapter 10 (1973).
Willan et al., FEBS Lett., 80:133–136 (1977).
O'Shannessy et al., 1984, Immunology Lett., 8:273–277.

AMINE DERIVATIVES OF FOLIC ACID ANALOGS

CROSS REFERENCE TO RELATED APPLICATIONS

This is a continuation of application Ser. No. 06/861,037 filed May 8, 1986, now abandoned which is a continuation-in-part application of copending applications Ser. Nos. 650,375, U.S. Pat. No. 4,867,973 and 650,754 filed on Sep. 13, 1984 now abandoned Ser. Nos. 646,327, now abandoned, 646,328 filed on Aug. 31, 1984, U.S. Pat. No. 4,741,900, and Ser. No. 356,315 filed on Mar. 9, 1982, now U.S. Pat. No. 4,671,958.

TABLE OF CONTENTS

1. Field of the Invention
2. Background of the Invention
   2.1 Derivatives of Methotrexate and Aninopterin
   2.2 Covalent Attachment of Methotrexate To Antibody Molecules
3. Summary of the Invention
4. Brief Description of the Figures
5. Definitions
6. Detailed Description of the Invention
   6.1. Amine Derivatives of Folic Acid Analogs
   6.2. Methods for Synthesis of Amine Derivatives of Folic Acid Analogs
   6.3. Methods for Preparing Antibody Conjugates
      6.3.1. Chemical Methods of Oxidation
      6.3.2. Enzymatic Method of Oxidation
      6.3.3. Coupling Oxidized Antibody and An Amine Derivative of a Folic Acid Analog
      6.3.4. Stabilization of the Antibody Conjugates
      6.3.5. Removal of Aggregates
   6.4. Uses of Amine Derivatives of Folic Acid Analogs and Antibody Conjugates
7. Preparation of Antibody-Folic Acid Analog Conjugates
   7.1. Synthesis of Amine Derivatives of Folic Acid Analogs
      7.1.1. Methotrexate-$\gamma$-Hydrazide (MTX-$\gamma$-HY) (1)
         7.1.1.1. Methotrexate-$\gamma$-Hydrazide (1) by the Mixed Anhydride Method: Method 1
         7.1.1.2. Methotrexate-$\gamma$-Hydrazide by Active Ester:
         7.1.1.3. Methotrexate-$\gamma$-Hydrazide from Methotrexate by Carbodiimide: Method 3
      7.1.2. Methotrexate-$\alpha$-Hydrazide (MTX-$\alpha$-Hy) (7)
      7.1.3. Methotrexate-$\alpha$-$\alpha$-Lysyl-Glycyl-Glycyl-Tyrosyl-Hydrazide.(11)
      7.1.4. Aminopterin-$\gamma$-Hydrazide (AM-$\gamma$-Hy) (16)
      7.1.5. Aminopterin-$\alpha$-Hy (AM-$\alpha$-HY) (19)
      7.1.6. Methotrexate-$\alpha$-$\alpha$-Lysine.(21)
   7.2 Preparation of Antibody Conjugates
      7.2.1. MTX-$\gamma$-Hy-Antibody
      7.2.2. MTX-$\alpha$-$\alpha$-Lysine-Antibody
8. Superior Therapeutic Effect of Site Selective MTX-$\gamma$-Hy-Antibody Conjugate
9. In Vitro Cleavage of MTX-$\alpha$-$\alpha$-Lysyl-Glycyl-Glycyl-Tyrosyl-NHN=Antibody Conjugate

1. FIELD OF THE INVENTION

The present invention relates to site selectively attached antibody-therapeutic agent conjugates. More particularly, the invention encompasses derivatives of folic acid analogs covalently attached to an antibody or antibody fragment via a reactive amine of the analog. Methods for preparing the antibody conjugates, as well as methods for using the antibody conjugates in vivo are described. Also encompassed are methods for synthesizing reactive amine-containing derivatives of folic acid analogs such as methotrexate and aminopterin.

2. BACKGROUND OF THE INVENTION

2.1. Derivatives of Methotrexate and Aminopterin

Rosowsky et al. (1981, J. Med. Chem 24: 1450, hereinafter "Rosowsky et al. I") describes a method for preparing hydrazide derivatives of methotrexate by coupling 4-amino-4-deoxy-$N^{10}$-methylpteroic acid (MAPA) to an appropriately protected L-glutamic acid precursor coupled by means of a peptide bond forming agent such as diethyl phosphorocyanidate followed by reaction with hydrazine and removal of the protective ester moiety. The MAPA can be prepared by known chemical synthetic methods [see e.g., Rosowsky et al., 1985, J. Med. Chem. (hereinafter "Rosowsky et al. II"); Chaykovsky et al., 1974, J. Med. Chem 17: 1212; Piper et al., 1977, J. Org. Chem. 42: 208] or by cleavage of methotrexate with carboxypeptidase $G_1$ (see Martinelli et al., 1979, J. Med. Chem. 22: 869; McCullough et al., 1971, J. Biol. Chem. 246: 720). According to the method of Rosowsky et al., I supra, L-glutamic acid-$\gamma$-methyl ester is esterified with t-butylacetate in the presence of 70% perchloric acid to form $\alpha$-t-butyl-$\gamma$-methyl glutamic acid. The C-protected $\alpha$-t-butyl-$\gamma$-methyl glutamic acid ester is condensed with MAPA, by heating MAPA with diethylphosphorocyanidate at about 80° C. for 2 minutes in dimethylformamide (DMF) containing triethylamine, then adding the glutamic acid derivative. Heating is continued at about 80° C. for another 2 hours, followed by solvent evaporation under reduced pressure and column chromatography on silica gel forming MTX-$\alpha$-t-butyl-$\gamma$-methyl ester. Reaction of the MTX-diester with hydrazine in methanol solution at 4° C. for 60 hours yields the $\alpha$-butyl ester $\gamma$-hydrazide. Acidolysis of the butyl ester in 1 N HCl at 50° C. for 1 hour, followed by ion-exchange chromatography on DEAE-cellulose forms the desired MTX-$\gamma$-hydrazide.

The method of Rosowsky et al. has a number of disadvantages including:

(1) the intermediate used, for example, $\alpha$-methyl ester-t-butyl glutamic acid is unstable as a free base, and (2) significant yields of aminopterin-$\alpha$-hydrazide could not be obtained using this method which utilizes the readily available MAPA analog 4-amino-4-deoxy-$N^{10}$-formyl pteroic acid because undesirable premature removal of the formyl protecting group from 4-amino-4-deoxy-$N^{10}$-formyl pteroic acid would occur during subsequent hydrazinoysis required to form the corresponding aminopterin analog.

A number of amino acid and peptide derivatives of methotrexate and/or aminopterin have been described. See, for example, Rosowsky, U.S. Pat. No. 4,490,529 entitled "Cysteic Acid and Homocysteic Acid Analogues of Methotrexate and Aminopterin"; Kempton et al, 1982, J. Med. Chem 25:475: Piper et al., 1982, J. Med. Chem. 25:182.

None of these references either describes or suggests that a reactive amine moiety of the attached amino acid or peptide might be useful for coupling the methotrexate or aminopterin analog to an antibody molecule via an oxidized carbohydrate moiety of the antibody.

2.2. Covalent Attachment Of Methotrexate To Antibody Molecules

A number of different reactions have been utilized to covalently attach methotrexate (or methotrexate analogs) to antibodies or antibody fragments. This has been accomplished by reaction of the amino acid residues of the antibody or antibody fragment, including amine groups of lysine residues, free carboxylic acid groups of glutamyl and aspartic residues, sulfhydryl groups of cysteinyl residues to carboxy, amino or sulfhydryl moieties of the drug compound. Methods involving attachment via amino acids which are regularly and randomly dispersed throughout the antibody molecule are referred to as random or non site-specific methods.

One of the most commonly employed random methods of covalent attachment is the carbodiimide reaction which links a carboxy (or amino) moiety of methorexate or a methotrexate analog to amino (or carboxy) moieties of an antibody. For example, Shen et al. describe coupling of methoxate (MTX) to human serum albumin via 1-ethyl-3-(3-dimethyl aminopropyl) carbodiimide thus forming a water-soluble MTX-HSA conjugate (1984, Proc. Nat'l Acad. Sci. U.S.A. 81 : 1445.

Kulkarni et al. (1981, Cancer Res. 41: 2700) describe the covalent attachment of MTX to an antibody molecule via three non site-specific methods: a carbodiimide procedure, a mixed anhydride reaction and an active ester method using reaction with N-hydroxysuccinimide esters of methotrexate. More recently, Kulkarni et al. (1985, Cancer Immunol. Immunother. 19: 211) describe conjugation of antibody or F(ab)$_2$ fragments and MTX via amino groups of lysines in the antibody using active esters of methotrexate.

Manabe et al. (1984, J. Clin. Med. 104: 445) describe covalent attachment of MTX to a monoclonal antibody via dextran T-40 which serves as a multivalent carrier. The dextran T-40 was oxidized using sodium periodate to form polyaldehyde-dextran. The aldehyde moieties of the oxidized dextran were then reacted with amino groups of the antibody molecule to form Schiff's bases (imines) or reduced Schiff's antibody intermediate and covalently attached conjugates were asserted to be formed by Schiff's base formation and subsequent reduction between aldehydes of the dextran and the 2 or 4 amino group of the MTX (Manabe et al., supra, at page 449). Applicants point out, however, that the 2 and 4 amino groups of methotrexate are poor nucleophiles and most probably cannot enter into Schiff's base or reduced Schiff's base formation as suggested.

All the above methods entail covalent attachment to the polypeptide backbone of an antibody molecule. Amino acids such as lysine, aspartic acid and glutamic acid that can be readily conjugated to drug moieties by conventional techniques occur relatively regularly and are randomly dispersed throughout the light and heavy chains of immunoglobulin molecules including the antigen binding region. Any chemical modification of the antigen binding region introduces changes in the recognition element of the antibody. Such modifications do change the affinity and specificity of the antibody for antigen. In a population of different antibodies, such alterations of the antigen binding region result in complete inactivation of some antibody molecules and in lesser degrees of inactivation of others depending upon the kind, severity and/or proximity of the alterations to the antigen binding region. This inactivation may be due to a change within or very near the antigen binding region, which alters the conformation of the binding site so as to make it unreactive, or may be due to a change in the region outside the antigen binding region, which limits access of antigen to the antigen binding region.

3. SUMMARY OF THE INVENTION

According to the general methods of the present invention, a therapeutic folic acid analog is covalently attached to an antibody or antibody fragment. The covalent attachment is accomplished so that the resulting antibody conjugate possesses both the ability to bind antigen and exert therapeutic effectiveness when administered in vivo. More specifically, the covalent attachment is accomplished by forming a covalent bond between an oxidized carbohydrate moiety of an antibody or antibody fragment and a reactive amine on a derivative of a folic acid analog in which the amine is selected from the group consisting of primary amine, secondary amine, hydrazine, hydrazide, phenylhydrazine, alkoxyamine, semicarbazide, and thiosemicarbazide.

In particular, the invention concerns methods for preparing therapeutic antibody-folic acid analog conjugates, comprising:

(a) reacting an antibody or antibody fragment with an oxidizing agent to form an aldehyde group in the carbohydrate moiety of the antibody or antibody fragment; and (b) reacting the aldehyde group of the oxidized carbohydrate moiety of the antibody or antibody fragment with a reactive amine group of a folic acid analog, said amine group selected from the group consisting of primary amine, secondary amine, hydrazine, hydrazide, alkoxyamine, phenylhydrazine, semicarbazide and thiosemicarbazide groups, to form a water-soluble antibody-folic acid analog conjugate having substantially the same immunoreactivity and immunospecificity as the unconjugated antibody or antibody fragment. Reduction can be used to stabilize the conjugate.

The invention further encompasses the antibody-folic acid conjugates which comprise a folic acid analog derivative attached via a covalent bond to an oxidized carbohydrate moiety of an antibody or antibody fragment, said water-soluble conjugate having substantially the same immunoreactivity or immunospecificity as the unconjugated antibody or antibody fragment and in which said covalent bond is selected from the group consisting of imine, enamine, hydrazone, phenylhydrazone, oxime, semicarbazone, thiosemicarbazone and reduced forms thereof.

Additionally the present invention encompasses novel reactive amine-containing folic acid analogs such as aminopterin-$\gamma$-hydrazide, aminopterin-$\alpha$-hydrazide, methotrexate-$\alpha$-hydrazide, and methotrexate-$\alpha$-$\alpha$-lysyl-glycyl-glycyl-tyrosyl-hydrazide useful to prepare the therapeutic antibody conjugates of the invention.

The invention also encompasses novel methods for synthesizing therapeutically effective amine derivatives of folic acid analogs, comprising the steps of:

(a) reacting a free carboxyl group of an N-protected L-glutamic acid having a protected carboxyl group and a free carboxyl group with a moiety containing a reactive amine or a protected reactive amine selected from the group consisting of primary amine, secondary amine, alkoxyamine, hydrazine, hydrazide, phenylhydrazine, semicarbazide and thiosemicarbazide to form an N-protected L-glutamic acid derivative containing a reactive amine or protected reactive amine;

(b) removing the N-protecting group from the N-protected L-glutamic acid derivative formed in step (a) to form an L-glutamic acid derivative containing a reactive amine or protected reactive amine with a free α-amino group;

(c) reacting the free α-amino group of the L-glutamic acid derivative formed in step (b) with an activated carboxyl group of either 4-amino-4-deoxy-$N^{10}$-methyl pteroic acid or 4-amino-4-deoxy-$N^{10}$-formyl pteroic acid, wherein said carboxyl group is activated by known carboxyl-activating agents; and (d) removing any protecting groups to form a reactive amine-containing, water-soluble derivative of either methotrexate or aminopterin wherein said derivative contains a reactive amine selected from the group consisting of primary amine, secondary amine, alkoxyamine, hydrazine, hydrazide, phenylhydrazine, semicarbazide and thiosemicarbazide.

The antibody-folic acid analogs of the present invention are ideally suited for in vivo therapy. Delivery of the folic acid analogs to specific target sites involves administering, to an animal or a human an effective amount of a water-soluble antibody-folic acid analog conjugate, wherein said conjugate is immunoreactive with and immunospecific for an antigenic determinant of said target site and substantially non-immunoreactive with and non-immunospecific for non-target sites and said antigenic determinant is not found in substantial amount in non-target sites. The target sites include specific cells, tissues, organs or any other sites in vivo which are associated with cellular disorders amenable to treatment with folic acid analogs.

The present invention encompasses methods for treating cellular disorders which comprise administering to an animal or a human, a therapeutically effective amount of a water-soluble site selectively attached antibody-folic acid analog conjugate prepared according to the invention. The cellular disorders which can be treated include but are not limited to the following: uterine choriocarinoma, chorioma, choriadenoma distruens, hydatidiform mole, acute and subacute leukemias, leukemic menigitis, lymphosarcoma, mycosis fungoides, lung cancers especially squamous and small cell types, osteogenic sarcoma, and certain tumors of the head, neck and pelvis.

4. BRIEF DESCRIPTION OF THE FIGURES

The present invention may be understood more fully by reference to the following detailed description of the invention, examples of specific embodiments of the invention, and the appended figures in which:

FIG. 1 is a graph illustrating the effect on an established BN tumor xenograft of injection of site selectively attached MTX-γ-Hy-antibody conjugate i.e. MTX-Hy-CYT015. Tumor growth in untreated control animals is also included for comparison.

Figure 2:
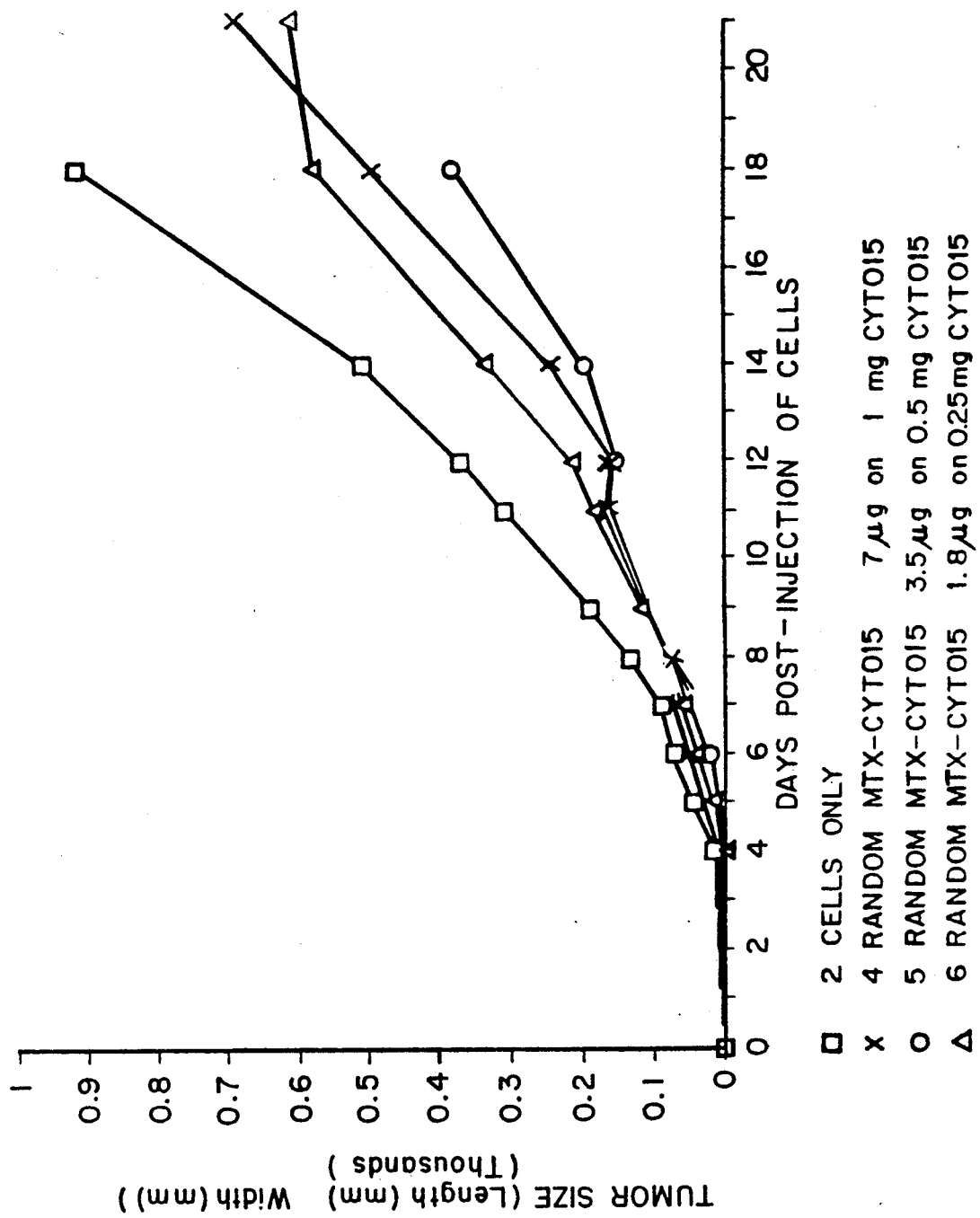

FIG. 2 is a graph illustrating the effect on an established BN tumor xenograft of injection of randomly attached MTX-antibody conjugate i.e. Random MTX-CYT015. Tumor growth in untreated control animals is included for comparison.

5. DEFINITIONS

As used throughout the instant specification the term "folic acid analog" is intended to encompass any analog of folic acid that contains at least one carboxyl group and that acts as an antimetabolite by interfering with normal folic acid dependent metabolic processes, thus producing the symptoms of a folic acid deficiency.

The term "amine derivative of folio acid" is intended to encompass any folic acid analog that contains or has been modified to contain a reactive amine.

The term "reactive amine" is intended to encompass any nitrogen-containing functional group that can be covalently attached or bonded through a nitrogen atom to an aldehyde functional group either by a simple chemical condensation reaction or by a chemical condensation reaction followed by reduction to stabilize the covalent bond formed Examples of such reactive amines include but are not limited to: primary amine, secondary amine, hydrazine, hydrazide, phenylhydrazine, alkoxyamine, semicarbazide and thiosemicarbazide.

6. DETAILED DESCRIPTION OF THE INVENTION

The present invention concerns water-soluble antibody-conjugates prepared by covalently attaching an amine derivative of a folic acid analog to an antibody or antibody fragment. The amine derivatives of folic acid analogs are selectively attached via a reactive amine group to carbohydrate moieties of an antibody molecule which are not part of nor directly involved with the antigenic site of the molecule. Thus after site selective attachment, the antibody conjugate has substantially the same immunoreactivity and immunospecificity as the unconjugated antibody or antibody fragment.

In one embodiment of the present invention, the reactive amine group is attached directly to a folic acid analog. As illustrative examples, a hydrazine group may be attached directly to either the α or γ carboxyl group of the glutamyl moiety of methotrexate or aminopterin. In another embodiment of the invention, the reactive amine group may be part of an attached linking moiety including but not limited to amino acids such as lysine, arginine, etc. and peptides such as tyrosyl-glycyl-glycyl-arginyl-ε-lysine in which a peptide terminating free amino group serves as the reactive amine.

The reactive amine groups are attached to the folic acid analogs so that when conjugated to antibodies and administered in vivo the antibody-folic acid analog conjugates are therapeutically effective against a variety of neoplastic conditions.

Antibodies used in the present invention may be conventional antibodies or monoclonal antibodies. Use of monoclonal antibodies offers several advantages because each monoclonal antibody is specific for one antigenic determinant and large amounts can easily be produced using known techniques.

Antibodies useful in the invention are directed against any target associated with cellular disorders which can be treated using the folic acid analogs. The term "cellular disorders" as used throughout this application is intended to encompass neoplasms and other hyperplastic conditions, whether benign or malignant, which are amendable to treatment using folic acid analogs as well as conditions such as rheumatoid arthritis which is amendable to treatment using folic acid analogs. Such cellular disorders include but are not limited to: uterine choriocarcinoma, chorioma, chorioadenoma destruens, hydatidiform mole, acute and subacute leukemias, leukemic menigitis, lymphosarcoma, mycosis fungoides, lung cancers particularly squamous and small cell types, osteogenic sarcoma, certain tumors of the head, neck and pelvis, severe disabling psoriasis and rheumatoid arthritis.

Since the folic acid analogs must be internalized into cells in order to exert antimetabolic effects, a crucial consideration for therapeutic effectiveness of an analog against a particular tumor is entry of the analog into tumor cells. For the most part, folic acid analogs are internalized into cells via carrier-mediated folate transport systems rather than via simple diffusion. In fact, certain tumor-types are resistant to folic acid analogs because the tumor cells are characterized by impaired folate transport systems (see Piper et al, 1982, J. Med. Chem. 25: 182). It is contemplated that the antibody-folic acid analog conjugates of the present invention might affect different receptor sites on cells and thus modify normal transport of the folic acid analog into tumor cells. Thus, it is further envisaged that attachment of a folic acid analog to an antibody specific for an antigen of a tumor resistant to the corresponding free analog may permit treatment of such resistant tumor with the antibody-folic acid conjugate. The following scheme Provides a convenient method for determining whether a specific tumor can effectively be treated in vivo using a particular antibody-folic acid analog conjuqate of the present invention:

A small sample of a tumor to be treated is obtained by conventional methods and divided into several aliquots. An antibody, either monoclonal or polyclonal, immunoreactive with and immunospecific for the particular tumor is identified and/or prepared using conventional or hybridoma techniques. An antibody-folic acid analog conjugate is prepared according to the present invention (see Section 6.3, infra). One aliquot of the tumor sample is inserted subcapsularly into the kidney of an experimental animal. Either a normal or nude mouse affords a convenient experimental animal model. The tumor fragment is measured, for example, using an ocular micrometer and the antibody-folic acid conjugate is administered intravenously for several days. Animals having a similarly implanted subrenal capsule tumor fragment but which are untreated serve as negative controls. Measurements are made periodically of the implanted tumor tissue and inhibition of tumor growth or reduction in tumor size of the treated animals indicates therapeutic effectiveness of the conjugates. Using the above scheme, any human tumor tissue can be screened for in vivo sensitivity to the antibody-folic acid conjugates of the invention.

Thus the term "cellular disorders" is further intended to encompass any neoplastic tumorous growth which is amenable to therapeutic treatment using the antibody-folic acid analog conjugates as determined by the above in vivo test.

Examples of targets associated with cellular disorders which can effectively be treated using the antibody conjugates of the invention include but are not limited to: tumor antigens, histocompatibility, differentiation and other cell membrane antigens, enzymes, hormone receptors, oncogene products, etc. Additionally a combination of antibodies reactive to different antigenic determinants may be used. Immunoglobulins which may be used as carriers include: certain classes of antibodies such as IgA, IgD, IgE, IgM; certain classes of IgG; or certain fragments of immunoglobulins, e.g., half antibody molecules (or single heavy: light chain pair), Fab, Fab' or (Fab')$_2$ fragments.

The reasons for the therapeutic effectiveness of the presently claimed antibody-folic acid analog conjugates when administered in vivo remain obscure, and a number of mechanisms seem plausible. Although not desiring to be limited to any particular theory to explain the therapeutic activity when conjugates of the invention are administered in vivo, applicants offer the following theoretical explanations.

According to one embodiment of the invention, an antibody conjugate is formed by covalent attachment via a reactive amine group covalently bonded to the $\gamma$-carboxyl group of the glutamyl moiety of the folic acid analog. It is possible that such attachment permits the $\alpha$-carboxyl group of the glutamyl moiety which is reported to be important for therapeutic efficacy, to retain its activity if the folic acid analog is not released in vivo from the antibody-folic acid analog conjugate.

According to another embodiment of the invention, a reactive amine group is covalently attached to the folic acid analog via a peptide, containing said amine, which peptide is susceptible to cleavage by an extracellularly active proteolytic enzyme. High concentrations of these proteolytic enzymes have been implicated at tumor sites. In this case, the peptide may be attached to either the $\alpha$ or $\gamma$ carboxyl group of the glutamyl moiety of the folic acid analog. It is possible that the therapeutic effectiveness of the antibody-folic acid conjugates prepared according to this embodiment is due to enzymatically catalyzed release of the active folic acid analogs as free drugs at the intended target in vivo. As an illustrative example, it is postulated that a methotrexate-antibody conjugate in which methotrexate is covalently attached, via the $\alpha$-carboxyl group of the glutamyl moiety, to lysyl-glycyl-glycyl-tyrosyl hydrazide which is attached to an aldehyde group of an oxidized antibody could be cleaved in vivo at a target site by enzymes such as plasmin and carboxypeptidase. Thus, therapeutically effective methotrexate would be enzymatically released at the intended target site in vivo. In fact, data demonstrating the enzymatically catalyzed cleavage of free methotrexate from a methotrexate-$\alpha$-$\alpha$-lysyl-glycyl-glycyl-tryosyl-hydrazide antibody conjugate forming free methotrexate in vitro is presented in Section 9, infra.

According to yet another embodiment of the invention, the folic acid analog is attached, either directly or by means of a linking peptide moiety, via a reactive amine which forms a covalent bond to the antibody which may be susceptible to chemical cleavage under conditions found in vivo at the target site. Thus, it is possible that the tree folic acid analog may be released in vivo either at the target site prior to uptake into tumor cells or perhaps at the target site even after uptake of the conjugate into tumor cells As an illustrative example, a hydrazone bond may be formed between methotrexate-$\gamma$-hydrazide and an aldehyde group of an oxidized antibody. Such hydrazone bond could be susceptible to in vivo slow hydrolysis, particularly if in vivo oxidation of the hydrazone occurs. It is postulated that such hydrolysis could occur either at the tumor cell surface after binding of the conjugate, or intracellularly after uptake of the conjugate. In either case, the free therapeutically active folic acid analog would be released in vivo.

The above alternate possibilities including therapeutic activity without release from the conjugate, enzymatically catalyzed release, and chemically induced release at an in vivo target are offered to explain the therapeutic effectiveness of the folic acid antibody conjugates of the invention in vivo. The invention, however, is not to be limited to any particular theory or mechanism for such therapeutic effectiveness.

6.1. Amine Derivatives Of Folic Acid Analogs

As defined in Section 5, folic acid analogs are analogs of folic acid that contain at least one carboxyl group and that act as antimetabolites by interfering with normal folic acid dependent metabolic processes, thus producing the symptoms of a folic acid deficiency. Table I presents a non-exhaustive list of examples of such folic acid analogs.

TABLE I
FOLIC ACID ANALOGS

Methotrexate
Aminopterin
3',5' Dichloromethotrexate
3',5' Dichloroaminopterin
5,8-Dideazamethotrexate
5,8 Dideaza 5,6,7,8-tetrahydromethotrexate
5,8-Dideaza 5,6,7,8-tetrahydroaminopterin
5,8,10-Trideazaaminopterin
5,10-Dideazatetrahydrofolic acid
8,10-Dideazaaminopterin Amine derivatives of these and other folic acid analogs are useful according to the present invention. Such amine derivatives encompass any folic acid analog containing or modified to contain a reactive amine moiety. The term "reactive amine" is intended to encompass any nitrogen-containing functional group that can be covalently attached or bonded through a nitrogen atom to an aldehyde functional group either by a single chemical condensation reaction or by a chemical condensation reaction followed by reduction to stabilize the covalent bond formed. Thus amine derivatives of folic acid analogs useful according to the invention include but are not limited to: methotrexate-γ-hydrazide, methotrexate-α-hydrazide, 3'5-dichloromethotrexate-γ-hydrazide, 3', 5-dichloromethotrexate-α-hydrazide, methotrexate-α-α-lysylglycyl-glycyl-tyrosyl hydrazide, methotrexate-γ-tyrosyl hydrazide, methotrexate-α-α-lysyl hydrazide, methotrexate-α-α-lysine, methotrexate-αα-lysyl-ε-arginine-glycine-glycine-tyrosine, aminopterin-γ-hydrazide, aminopterin-α-hydrazide, 3'5'-dichloraminopterin-γ-hydrazide, 3'5'-dichloroaminopterin-α-hydrazide, aminopterin-γ-tyrosyl hydrazide, aminopterin-α-α-lysyl-glycyl-tyrosyl hydrazide, aminopterin-α-α-lysyl hydrazide, aminopterin-α-α-lysine, and aminopterin-α-α-lysyl-ε-arginine-glycine-glycine-tyrosine. Reactive amine-containing derivatives of folic acid analogs such as 5,8-dideazamethotrexate, 5,8-dideaza 5,6,7,8-tetrahydromethotrexate, 5,8,-dideaza 5,6,7,8-tetrahydroaminopterin, 5,8,10-trideazatetrahydrofolic acid, and 8,10-dideazaaminopterin are also useful according to the invention.

6.2. Methods For Synthesis Of Amine Derivatives Of Folic Acid Analogs

The amine derivatives of folic acid analogs used to form the antibody conjugates of the invention can be synthesized using a variety of methods.

According to one method of the invention, a folic acid analog containing a carboxyl group is activated by reaction with a activating agent such as carbodiimide. The activated intermediate is reacted with a suitable nucleophile such as hydrazine or a diamine to yield a reactive amine-containing folic acid analog which has the capacity to bind via said reactive amine to an aldehyde moiety of an oxidized antibody. Alternatively, the activated intermediate is reacted with an amino acid or a peptide containing a protected reactive amine, which is deprotected following reaction with the carboxyl group, to yield a reactive amine-containing folic acid analog which has the capacity to bind via said reactive amine to an aldehyde moiety of an oxidized antibody. Since some of the folic acid analogs have a glutamyl moiety containing two different carboxyl groups that can be derivatized in this manner, isomeric mixtures of products result depending upon the nature of the nucleophile. The desired isomer should be separable from the undesirable positional isomers using conventional techniques. (For an experimental demonstration of the synthesis of methotrexate-γ-hydrazide using this method see Section 7.1.3 infra.)

According to another novel method of the invention an amine derivative of folic acid analogs such as methotrexate and aminopterin can be synthesized as follows.

A glutamic acid derivative containing a protected reactive amine is first prepared. A preferred starting material is a glutamic acid derivative in which the α-amino group is protected for example, by a carbobenzyloxy (CBZ) or an fluroenylmethoxycarbonyl (Fmoc) moiety, and in which one of the carboxyl groups is protected, for example, by an ester moiety such as t-butyl ester. The other carboxyl group of the protected glutamic acid is attached to a moiety containing a reactive amine or a protected reactive amine selected from the group consisting of primary amine, secondary amine, hydrazine, hydrazide, phenylhydrazine, alkoxyamine, semicarbazide and thiosemicarbazide and their protected derivatives. The reactive amine-containing moiety can be attached to the free carboxyl of the protected glutamic acid by known carboxyl activation methods such as the coupling by carbodiimides, mixed anhydrides or active esters. If the reactive moiety is a hydrazine, it is preferred to further protect this moiety, for example using a butoxycarbonyl (Boc) blocking group.

The α-amino group of the N-protected L-glutamic acid derivative containing a reactive amine or a protected reactive amine is deprotected to yield the free α-amino derivative. The free α-amino group is coupled to carboxyl group of either 4-amino-4 deoxy-$N^{10}$-methyl pteroic acid (MAPA) or 4-amino-4 deoxy-$N^{10}$-formyl pteroic acid (FAPA) by known carboxyl activation methods such as coupling by carbodiimides, mixed anhydrides or active esters. After removal of any protecting groups, the product formed is reactive amine-containing water-soluble derivative of either of the folic acid analogs methotrexate or aminopterin.

This method of coupling a reactive amine containing- (or a protected-reactive amine containing-) glutamic acid derivative to a pteridinyl amino benzoic acid can be generalized to yield a variety of reactive amine-containing folic acid analogs by utilization of the appropriately substituted benzoyl moiety in place of either MAPA or FAPA. For example, a substituted benzoic acid such as 4-amino-4-deoxy-8,10-dideaza pteroic can be substituted for MAPA in the methods above to yield a reactive amine derivative of 8,10-dideazaaminopterin, a potent folic acid analog (De Graw et al., 1984, J. Med. Chem. 27:376).

By way of illustration, methotrexate-γ-hydrazide can be prepared according to the novel method of the invention as follows:

Commercially available L-glutamic acid α-t-butyl ester is protected as its N-Fmoc derivative by reaction with one equivalent of fluorenylmethyl succinimidyl carbonate in a 1:1 aqueous:acetone solution containing 1 equivalent of $NaHCO_3$ at room temperature overnight. The Fmoc L-glutamic α-t-butyl ester is isolated after acidification, extraction with ether, and evaporation of the organic solvent. The Fmoc L-glutamic acid α-t-butyl ester is dissolved in dry dimethylformamide (DMF) with 1-3 equivalents of 2,4-dinitrophenol followed by 1-3 equivalents of 3(3-dimethylaminopropyl) 1-ethylcarbodiimide hydrocholoride. The resultant mixture is stirred for about 24 hours at room temperature. The progress of the reaction is monitored by thin layer chromatography (TLC). The reaction mixture can be heated to about 50° C. if necessary to complete the reaction.

After complete formation of the 2,4-dinitrophenyl active ester, about 1-3 equivalents of t-butyl carbazate is added and the reaction mixture incubated at room temperature for about 24 hours with stirring. Evaporation of the solvent is followed by extraction of the reaction mixture with ether:water. Separation of the layers and washing of the ether layer with cold dilute $NaHCO_3$ solution and subsequent drying and evaporation of the ether layer yields Fmoc L-glutamic acid α-t-butyl ester-γ-N'-Boc-hydrazide. Removal of the Fmoc protecting group with about 10% diethylamine in tetrahydrofuran (THF) followed by evaporation of the diethylamine and THF yields the crude L-glutamic acid α-t-butyl ester-γ-N'-Boc-hydrazide. This crude L-glutamic acid derivative is used without further purification.

MAPA can be suspended in dry DMF with about 1-4 equivalents of 2,4-dinitrophenol. 3(3-Dimethylaminopropyl) 1-ethylcarbodiimide (about 1-5 equivalents) is added and the reaction mixture stirred at room temperature for about 2 hours. The progress of the reaction is monitored by TLC and the reaction mixture is heated to not greater 50° C. to complete the reaction, if necessary Subsequent evaporation of the solvent and trituration with isopropanol affords the solid MAPA-2,4-dinitrophenyl ester.

The MAPA-2,4-dinitrophenyl ester is dissolved in dry DMF along with about 1-3 equivalents of L-glutamic acid α-t-butyl ester-γ-N'-Boc hydrazide and about 1-3 equivalents of disopropylethylamine. The reaction mixture is stirred for about 24 hours at room temperature. The progress of the reaction is monitored by TLC and heated, if necessary, to no greater than 50° C. to complete the reaction. The mixture is evaporated and crude product chromatographed on silica gel to yield methotrexate-γ-t-butyl ester-γ-N'-Boc-hydrazide. Subsequent deprotection with about 30% trifluoroacetic acid in methylene chloride for about 1 hour at room temperature, followed by evaporation yields a crude trifluoroacetate salt of methotrexate-γ-hydrazide which is subsequently neutralized using ammonium bicarbonate solution. Ion exchange chromatography, for example, using QAE Sephadex ® with an ammonium bicarbonate gradient followed by lyophillization yields methotrexate-γ-hydrazide.

The above method of the present invention can be modified by those with ordinary skill in the art using appropriately substituted benzoic acid components in place of the MAPA moiety. Hence the invention is intended to encompass such modifications to yield reactive amine-containing derivatives of other folic acid analogs.

The novel methods of the present invention for synthesis of amine derivatives of folic acid analogs offer the following advantages over conventional methods:

(1) The present method allows utilization of the readily available aminopterin Precursor 4-amino 4-deoxy-$N^{10}$-formyl pteroic acid to form the hydrazide derivative of aminopterin and thus provides a method for high yield, isomerically pure preparation of the novel compound of the invention aminopterin hydrazide. Because the formamide protecting group is readily removed by reaction with hydrazine or hydrazine derivatives (see Geiger et al., 1968, Chem. Ber. 101: 33386) use of conventional methods for the synthesis of hydrazides of folic acid analogs (see Rosowsky et al.I, supra) which require hydrazinolysis to prepare hydrazide derivatives of aminopterin would lead to undesirable premature removal of the protecting $N^{10}$- formyl group. Thus, comparable yields of aminopterin-γ-hydrazide or aminopterin-α-hydrazide could not be expected using conventional methods.

(2) When the desired product is methotrexate-hydrazide, the present method yields a more non-polar and organic solvent soluble derivative as the penultimate precursor to the methotrexate-hydrazide. The method allows simple purification of the penultimate precursor by standard chromatographic techniques using organic solvent systems. This results in the enhanced likelihood of formation of a purer methotrexate-hydrazide in the ultimate step of the synthesis.

Alternatively, the method of Rosowsky et al. (1981, J. Med. Chem 24:1450) is also useful to synthesize reactive amine derivatives of folic acid analogs useful according to the present invention. For example, as detailed in Section 2.1, methotrexate-γ-hydrazide can be synthesized using MAPA and an appropriately protected L-glutamic acid ester derivative coupled by means of a peptide bond forming agent such as diethyl phosphorocyanidate. Subsequent hydrazinolysis followed by removal of the protecting groups affords a reactive amine-containing folic acid analog which has the capacity to bind via said reactive amine to an aldehyde moiety of an oxidized antibody.

6.3 Methods For Preparing Antibody Conjugates

Since antibodies are glycoproteins, compounds may be attached to the carbohydrate moiety covalently attached to the peptide backbone of the molecule. Some of the carbohydrate moieties are located on the Fc region of the immunoglobulin and are required for bonding of components of the complement system to occur. The carbohydrate moiety of the Fc region of an immunoglobulin may be utilized in the scheme described herein. Alternatively, the Fab or Fab' fragments of any immunoglobulins which contain carbohydrate moieties may be utilized in the reaction scheme described herein. An example of such an immunoglobulin is the human IgM sequenced by Putnam et al. (1973, Science 182: 287).

As explained in detail below, the carbohydrate side chains of antibodies or antibody fragments may be selectively oxidized to generate aldehydes. The resulting aldehyde may then be reacted with amine groups (e.g., ammonia derivatives such as primary amine, secondary amine, alkoxyamine, hydrazine, hydrazide, phenylhydrazine, semicarbazide or thiosemicarbazide) to form an imine, enamine, oxime, hydrazone, phenylhydrazone, semicarbazone, thiosemicarbazone or reduced forms thereof.

Alternatively, the carbohydrate moiety of the antibody may be modified by enzymatic techniques so as to enable attachment to or reaction with amine groups. For example, neuraminidase plus galactose oxidase may be used to form an aldehyde moiety.

6.3.1. Chemical Methods Of Oxidation

Oxidation of the carbohydrate portion or moiety of antibody molecules leads to formation of aldehyde groups. A variety of oxidizing agents can be used, such as periodic acid, paraperiodic acid, sodium metaperiodate and potassium metaperiodate. Among these, oxygen acids and salts thereof are preferred since secondary or undesirable side reactions are less frequent. For a general discussion, see Jackson, 1944, in Organic Reactions 2, p.341; Bunton, 1965, Oxidation in Organic Chemistry, Vol. 1 Wiberg, ed., Academic Press, New York, p.367.

Oxidation of antibodies with these oxidizing agents can be carried out by known methods. In the oxidation, the antibody is used generally in the form of an aqueous solution, the concentration being generally less than 100 mg/ml, preferably 1 to 20 mg/ml. When an oxygen acid or salt thereof is used as the oxidizing agent, it is used generally in the form of an aqueous solution, and the concentration is generally 0.001 to 10 mM and preferably 1.0 to 10 mM. The amount of the oxygen acid or salt thereof depends on the kind of antibody, but generally it is used in excess, for example, ten to 100 times as much as the amount of the oxidizable carbohydrate. The optimal amount, however, can be determined by routine experimentation.

In the process for oxidizing antibodies with oxygen acids or salts thereof, the optional ranges include a pH from about 4 to 8, a temperature of from 0° to 37° C., and a reaction period of from about 15 minutes to 12 hours.

During the oxidation of the glycoprotein with an oxygen acid or a salt thereof, light is preferably excluded to prevent overoxidation of the glycoprotein.

6.3.2. Enzymatic Method Of Oxidation

Oxidation of the carbohydrate portion of antibody molecules may also be accomplished using the enzyme galactose oxidase (Cooper et al., 1959, J. Biol. Chem. 234: 445) with or without neuraminidase. The antibody is used in aqueous solution, the concentration being generally 0.5 to 20 mg/ml. The enzyme generally is used at pH about 5.5 to about 8.0. The influence of pH, substrate concentration, buffers and buffer concentrations on enzyme reaction are reported in Cooper et al., supra.

6.3.3. Coupling Oxidized Antibody and an Amine Derivative of a Folic Acid Analog The antibody conjugates of the invention are produced by reacting the oxidized antibody with a folic acid analog having an available amine group selected from the group consisting of primary amine, secondary amine, hydrazine, hydrazide, alkoxyamine, phenylhydrazine, semicarbazide and thiosemicarbazide groups. The immediately resulting products contain a carbon-nitrogen double bond resulting from elimination of a molecule of water from the initial addition products:

For a general discussion of the reaction of aldehydes with hydrazides, see March, 1978, in Advanced Organic Chemistry: Reactions Mechanisms and Structure, McGraw Hill Co., New York, pp. 824–825.

A solution of the oxidized antibody at a concentration from about 0.5 to 20 mg/ml is mixed with an amine derivative of folic acid (molar ratios of reactive amine group to antibody aldehyde ranging from about 1 to about 10,000) and the solution incubated for from about 1 to 18 hours. Suitable temperatures are from 0° to 37° C. and pH may be from about 6 to 8.

6.3.4. Stabilization of the Antibody Conjugates

After the antibody conjugates have been formed between the antibody and the folic acid analog as described in Section 5.3.3. they can optionally be stabilized with a suitable reducing agent, such as sodium cyanoborohydride or sodium borohydride:

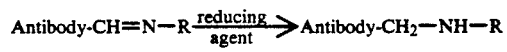

Reducing agent is generally added to a molar excess of from about 10 to 100 fold molar excess over available aldehyde groups. For a general discussion, see Jentoft and Dearborn, (1979, J. Biol. Chem. 254: 4359).

6.3.5. Removal of Aggregates

According to one embodiment of the present invention, the reactive amine group of the derivatized folic acid analog which is covalently attached to the aldehyde group of an antibody or antibody fragment carbohydrate moiety is a primary amine. The resulting antibody conjugates may contain aggregates formed by intramolecular Schiff's base formation between primary amines of amino acids and the aldehyde moieties of the antibody molecule. Thus in these instances, any aggregates formed are optionally removed from the desired antibody conjugates by suitable gel filtration methods including but not limited to high performance gel permeation liquid chromatography. Removal of undesirable aggregates is particularly important because the antibody conjugates are used in vivo to deliver the attached therapeutic folic acid analog to a desired target site. Any such antibody aggregates would be taken up by the reticuloendothelial system for removal, and such transport away from the target site or specific tissue would diminish the degree of localization and hence therapeutic effectiveness of the folic acid analog conjugates administered, as well as potentially leading to toxic effects on non-target sites.

6.4. Uses of Amine Derivatives of Folic Acid Analogs and Antibody Conjugates The amine derivatives of folic acid analogs of the present invention are particularly well suited for use in the preparation of therapeutic antibody conjugates. Thus, these derivatives represent intermediates in the preparation of therapeutic antibody-folic acid analog conjugates. Selective attachment of the folic acid analogs via a reactive amine to an oxidized carbohydrate moiety of an antibody or antibody fragment results in a conjugate that retains the antibody specificity and immunoreactivity.

The antibody conjugates of the invention are ideally suited for use in methods of in vivo therapeutic treatment of cellular disorders. Such methods comprise administering a therapeutically effective amount of an antibody-folic acid analog conjugate of the invention, said conjugate being immunoreactive with and immunospecific for a target site associated with said cellular disorder and substantially non-immunoreactive with and non-immunospecific for tissue not associated with said cellular disorder. The conjugates of the invention are therapeutically effective for treating cellular disorders amenable to treatment with the non-amine containing folic acid analog precursors from which the conjugates are derived.

The cellular disorders for which the antibody-conjugates of the present invention are particularly useful include but are not limited to the following: uterine choriocarinoma, chorioma, choriadenoma distruens, hydatidiform mole, acute and subacute leukemias, leukemic meningitis, lymphosarcoma, mycosis fungoides, lung cancers especially squamous and small cell types, osteogenic sarcoma, certain tumors of the head, neck and pelvis.

Additionally, it is envisaged that the folic acid analogs may be useful for treatment of tumors that are resistant to the free folic acid analog from which the amine derivative is derived. To determine whether a particular tumor may be therapeutically treated in vivo using a specific antibody-folic acid conjugate of the invention, the following in vivo test may be utilized: A small sample of a tumor to be treated is obtained by conventional methods and divided into several aliquots. An antibody, either monoclonal or polyclonal, immunoreactive with and immunospecific for the particular tumor is identified and/or prepared using conventional or hybridoma techniques. An antibody-folic acid analog conjugate is prepared according to the present invention. One aliquot of the tumor sample is inserted subcapsularly into the kidney of an experimental animal. Either a normal or nude mouse affords a convenient experimental animal model. The tumor fragment is measured, for example, using an ocular micrometer and the antibody-folic acid conjugate is administered intravenously for several days. Animals having a similarly implanted subrenal capsule tumor fragment but which are untreated serve as negative controls. Measurements are made periodically of the implanted tumor tissue and inhibition of tumor growth or reduction in tumor size of the treated animals indicates therapeutic effectiveness of the conjugates. Using the above scheme, any fresh human tumor tissue can be screened for in vivo sensitivity to the antibody-folic acid conjugates of the invention.

In vivo administration may involve use of pharmaceutical compositions of the antibody-folic acid analog conjugates in any suitable carrier, including serum or physiological saline, with or without another protein such as human serum albumin. Dosages of the conjugates may be readily determined by one of ordinary skill and may differ depending upon the nature of the cellular disorder and the Particular folic acid analog employed. The preferred mode of administration is generally parenteral via intramuscular, intravenous, intraarterial, intrathecal, intraperitoneal and intralymphatic routes.

The following series of Examples are presented for purposes of illustration and not by way of limitation on the scope of the invention.

7. Preparation of Antibody-Folic Acid Analog Conjugates

7.1. Synthesis of Amine Derivatives of Folic Acid Analogs

7.1.1. Methotrexate-γ-Hydrazide (MTX-γ-HY) (1)

N-4(((2,4-Diamino-6-pteridinyl)methyl)methylamino) benzoyl-L-glutamic acid-5-hydrazide (CAS Registry No. 79640-75-8) commonly termed "methotrexate-γ-hydrazide" was synthesized according to the present invention by a number of different methods illustrated below.

N-CBZ-L-glutamic acid α-t-butyl ester γ-N'-BOC-hydrazide (2)

The N-CBZ-L-glutamic acid-α-t-butyl ester -γ-dicyclohexyl amine salt (Bachem) was converted to the free acid by the method of Spannenberg et al., 1971, HoppeSeyler's Z. Physical Chem. 352:655. Alternatively, the free acid could be prepared using conventional methods by adding a CBZ moiety to commercially available L-glutamic acid-α-t-butyl ester. The free acid (0.93 gm, 3.0 mmoles) was dissolved in dry tetrahydrofuran (50 ml) under $N_2$ gas and cooled to 0° C. in an ice-water bath. N-Methyl morpholine (0.3 gm, 0.33 ml, 3.0 mmoles) was added. Isobutyl chloroformate (0.41 gm, 0.39 ml, 3.0 mmoles) was added dropwise with a syringe over the course of 15 minutes. After complete addition of the chloroformate, the reaction mixture was stirred for another 5 minutes at 0° C. while a slight turbidity developed. t-Butyl carbazate (0.40 gm, 3.0 mmoles) was added all at once and the reaction mixture was stirred overnight at room temperature. The reaction mixture was poured into water and extracted three times with ether. The ether extracts were combined and washed with saturated NaCl solution, dried with $Na_2SO_4$, then evaporated to give 1.13 gm (83%) of an oil which had the following characteristics using thin layer chromotography (TLC) and [$^1$HNMR] [(Merck silica gel, methylene chloride:methanol, ($CH_2Cl_2$:MeOH) 9:1) $R_f$=0.58; $^1$HNMR ($CDCl_3$, TMS) δ7.33(s, 5H), 5.10 (s, 2H) 4.50–4.15 (m, 1H), 2.60–1.80 (m, 4H), 1.46 (s, 18H).

L-Glutamic acid α-t-butyl ester γ-N'-BOC-hydrazide (3)

N-CBZ-L-glutamic acid α-t-butyl-ester γ-N'-Bochydrazide (1.13 gm, 2.5 mmoles) was dissolved in 200 ml absolute ethanol in a 500 ml Parr pressure bottle and 2.0 ml of acetic acid was added followed by 0.15 gm of 10% Pd on carbon. The solution was hydrogenated with monitoring by TLC (ninhydrin). When the reaction was complete (about 48 hours) the solution was filtered through Celite, evaporated and suspended in water. The water solution was extracted with methylene chloride, the layers separated, and the water layer lyophilized to give 0.52 gm (52%) of the free amino ester. $^1$HNMR ($CDCL_3$, TMS) δ6.8–6.4 (br d, 2H) 4.40–4.0(m, 1H) 2.8–2.1(m, 4H) 1.64–1.35(br d,18H).

N-Fluorenylmethoxycarbonyl(FMOC)-L-Glutamic acid-α-t-butyl ester (4)

Glutamic acid α-t-butyl ester (Chemical Dynamics, South Plainfield, N.J., 3.0 gm, 0.15 mmoles) was dissolved in acetone (60 ml). Sodium bicarbonate (1.24 gm, 15 mmoles) was dissolved in 60 ml water and added to the acetone solution. Fluorenylmethyl-succinimidyl-carbonate (Fluka, Hauppauge, N.Y.) (4.98 gm, 15 mmoles) was added to the solution and the reaction mixture stirred overnight at room temperature. Thin layer chromatography (Merck silica gel, $CH_2Cl_2$:MeOH, 9:1) indicated complete disappearance of the ninhydrin-positive spot at the origin and the appearance of a new fluorescent spot at $R_f=0.57$. The reaction mixture was evaporated and water (100 ml) was added to the reaction vessel. The aqueous suspension was extracted with three portions of ethyl ether and the combined ether layers washed with water, saturated NaCl solution and dried over $Na_2SO_4$. Evaporation of the ether gave 5.71 gm(91%) of a foamy solid which had the following spectrum: $^1$HNMR ($CDCl_3$, TMS) $\delta$7.9–7.20 (m, 8H) 5.80–5.40 (m, 1H), 4.55–4.05 (m, 4H) 2.66–1.72 (m, 4H) 1.41 (s, 6H).

N-FMOC-L-Glutamic acid-α-t-butyl ester-γ-N'-Boc-hydrazide (5)

N-Fmoc-L-glutamic acid-α-t-butyl ester (5.21 gm, 12.3 mmoles was dissolved in 250 ml of dry DMF under $N_2$ gas.2,4-Dinitrophenol (2.27 gm, 12.3 mmoles) was added followed by 1-ethyl-3(3-dimethylaminopropyl) carbodiimide hydrochloride. The reaction mixture was stirred at room temperature overnight. Analysis using TLC (Merck silica gel, $CH_2Cl_2$:MeOH; 9.1) showed complete disappearance of the starting material ($R_f=0.57$) and appearance of a new fluorescent spot at ($R_f=9$). t-Butyl carbazate (1.63 gm, 12.3 mmoles) was added at once and the reaction mixture incubated overnight at room temperature with stirring. The solvent was evaporated and the residue taken up in ethyl ether and washed with cold 5% $NaHCO_3$ solution until all the dinitrophenol was removed. The ether layer was washed with saturated NaCl solution, dried with $Na_2SO_4$ and evaporated to yield a foamy solid which was flash chromatographed on silica gel (petroleum ether-:ethyl acetate 1:1) to yield 4.19 gm (63%) of a foamy white solid having the following characteristics: $^1$HNMR ($CDCl_3$, TMS) $\delta$8.42(br s, NH), 7.90–7.20 (m, 8H) 6.88 (br s, NH) 5.90 (br d, NH) 4.60–4.05 (m, 4H) 2.60–1.95 (m, 4H) 1.42 (s, 18H).

4-Amino-4-deoxy-$N^{10}$-methyl pteroic acid-2,4-dinitrophenyl ester (6)

4-Amino-4-deoxy-$N^{10}$-methyl pteroic acid (MAPA)(0.98 gm, 3.0 mmoles) was suspended in 100 ml of dry DMF along with 0.83 gm (4.5 mmoles) of 2,4.dinitrophenol. 3-(3-Dimethyl aminopropyl)-1-ethyl carbodiimide hydrochloride (0.86 gm, 4.5 mmoles) was added and the solution stirred for about 72 hours. The disappearance of MAPA ($R_f=0.23$) and the appearance of the 2,4-dinitrophenyl ester (($R_f=0.49$) was monitored using TLC (Merck silica gel, $CHCl_3$:MeOH:HOAc; 9:1:0.5). Additional carbodiimide and 2,4-dinitrophenol was added in 1.5 mmole portions every 24 hours in order to get complete reaction of the MAPA starting material. Careful heating to no greater than about 50° C. promoted the reaction. When the starting MAPA was consumed, the reaction mixture was evaporated, and the residue was triturated with isopropanol to remove the residual carbodiimide, 2,4-dinitrophenol and any urea formed. The yellow solid (yield 90–100%) was homogeneous by TLC and gave the following NMR spectrum ($d_6$DMSO TMS) $\delta$9.0–8.5(m, 3H) 8.15–7.80 (m, 5H) 7.2–6.9 (m, 4H), 4.95 (br s, 2H) 3.33 (s, 3H).

7.1.1.1. Methotrexate-γ-Hydrazide (1) By the Mixed Anhydride Method: Method 1

7.1.1.1. Methotrexate-γ-Hydrazide (1) By The Mixed Anhydride Method:Method 1

MAPA (Rosowsky et al., 1985, J. Med. Chem 28: 660–667) (0.52 gm, 1.6 mmoles) was suspended in dry dimethyl formamide (100 ml, DMF) and disopropyl ethyl amine (0.41 gm, 0.56 ml, 3.2 mmoles) was added. Diethyl phosphorocyanidate (0.52 gm, 0.49 ml, 3.2 mmoles) was added and the reaction mixture stirred at room temperature for 1 hour. L-Glutamic acid α-t-butyl ester-γ-N'-Boc hydrazide (0.51 gm, 1.6 mmoles) was then added and the reaction stirred for 24 hours at room temperature. The solution was then rotary evaporated and flash chromatographed on silica gel using methylene chloride:methanol:acetic acid ($CH_2Cl_2$:MeOH:-HOAC; 9:1:0.5) to separate the products. The major product, with $R_f=0.48$ ($CH_2Cl_2$ MeOH; 9:1) was dried, then redissolved in 10 ml $CH_2Cl_2$ and 10 ml of trifluoracetic and stirred for 2 hours. The solution was evaporated, redissolved in water, adjusted to pH 12, and filtered. After the pH was adjusted to 8.0 with acetic acid, the filtrate was lyophylized. The resulting yellow residue was suspended in dry DMF, stirred for 3 hours and then filtered. The filtrate was evaporated to form a water soluble yellow powder which was predominately a single peak on reverse phase HPLC. Retention time was comparable to a methotrexate-γ-hydrazide prepared according to the method of Rosowsky, supra (a gift from Dr. A. Rosowsky, Dana Farber Cancer Research Institute, Boston, Mass.).

7.1.1.2. Methotrexate-γ-Hydrazine (1) By Active Ester: Method 2

N-Fmoc-L-glutamic acid α-t-butyl ester γ-N'-Boc-hydrazide (1.0 gm, 1.86 mmoles) was dissolved in 30 ml of dry tetrahydrofuran. Diethyl amine (5 ml) was added and the reaction mixture stirred at room temperature for 2 hours. Thin layer chromatography (Merck silica gel, $CHCl_3$: MeOH:$CH_2COOH$; 0:1:.5) revealed disappearance of the starting material ($R_f=0.78$) and the appearance of a new ninhydrin positive spot ($R_f=13$). The solution was evaporated and placed under vacuum at room temperature for 2 hours to remove the last traces of diethyl amine. The oily product thus formed, L-glutamic acid α-t-butyl ester γ-N'-Boc-hydrazide—was not isolated.

Crude L-glutamic acid α-t-butyl ester γ-N'-Boc-hydrazide was dissolved in 100 ml of dry DMF and 4-amino-4-deoxy-$N^{10}$-methylpteroic acid 2,4-dinitrophenyl ester (6) (0.91 gm, 1.86 mmoles) was added along with diisopropyl ethylamine (0.23 gm, 0.32 ml, 1.86 mmoles). The reaction mixture was stirred at room temperature for 24 hours then heated to 40° C. to effect complete reaction. The mixture was evaporated and the yellow crude oil product was flash chromatographed on silica gel ($CH_2Cl_2$:MeOH:HOAC, 9:1:0.5) to give 1.0 gm (86%) of a yellow solid which was homogenous by silica gel TLC ($CH_2Cl_2$:MeOH:HOAC, 9:1:0.5) and had the following NMR characteristics: $^1$HNMR ($CDCl_3$-$d_6$ DMSO, TMS) $\delta$9.43 (br s, 1H), 8.72 (s, 2H, $NH_2$), 8.40 (br d,1H) 7.95 (d, 2H), 7.74 (s, 2H, $NH_2$), 7.38 (d, 2H), 6.03 (s, 2H) 5.22 (s, 2H), 4.43 (m, 1H), 2.20–2.03 (m, 4H), 1.45 (s, 9H), 1.43 (s, 9H).

The yellow product above (0.42 gm) was dissolved in 10 ml dry $CH_2Cl_2$ and 5 ml of trifluoroacetic acid was added. The reaction mixture was stirred for 1 hour then evaporated to dryness. The yellow oily product was suspended in 100 ml of 0.025 M $NH_4HCO_2$ and 0.5M $NH_4HCO_3$ was added dropwise (about 20 drops) to effect almost complete solution. The yellow solution was chromatographed on 15 gm QAE Sephadex® (Sigma Chemical Company, St. Louis, Mo.) using 1 L of 0.025 M $NH_4HCO_3$ and followed by gradient elution with 1.5 L of 0.025 M $NH_4HCO_3$ and 1.5 L of 0.50M $NH_4HCO_3$. The yellow product which was eluted in the middle of the gradient was collected and lyophilized to yield methotrexate-γ-hydrazide which gave correct element analysis (C,H,N) for a trihydrate and compared favorably on HPLC ($C_{10}$) with a sample of methotrexate-γ-hydrazide prepared according to the method of Rosowsky, supra.

7.1.1.3. Methotrexate-γ-Hydrazine (1) From Methotrexate By Carbodiimide: Method 3

Methotrexate (0.5 gm, 1.1 mmole) was dissolved in dry DMF (50 ml) and 3(3-dimethylaminopropyl)-1-ethyl carbodiimide hydrochloride (0.42 gm, 2.1 mmoles) was added. The reaction mixture was incubated with stirring at room temperature for an additional 24 hours. Evaporation of the solvent left a yellow oil which was chromatographed on QAE Sephadex® (Sigma Chemical Company, St. Louis, Mo.), to give the yellow product methotrexate γ-hydrazide along with other products, presumably including, but not limited to MTX-α-hydrazide, etc , which could be separated from the desired MTX-γ-Hy by conventional preparative HPLC chromatographic techniques.

7.1.2. Methotrexate-α-Hydrazide (7) N-α-FMOC L-Glutamic acid N'-Boc-hydrazide γ-t-butyl ester (8)

N-α-Fmoc L-glutamic acid γ-t-butyl ester (5.0 gm, 12 mmoles) (Bachem) was dissolved in 100 ml of dry THF along with N-methyl morpholine (1.19 gm, 1.29 ml, 12 mmoles). The solution was cooled to 0° C. under nitrogen and then 2,2,2-tricloro-1,1-diethylchloroformate (3.39 gm, 1.4 mmoles) dissolved in 10 ml of dry THF was added dropwise over 10 minutes. After complete addition of the chloroformate, the reaction mixture was stirred at 0° C. for 15 minutes and then t-butyl carbazate (2.34 gm, 18 mmoles) was added and the reaction stirred for 10 more minutes at 0° C. then warmed to room temperature and stirred overnight. The solvent was evaporated and the reaction mixture was poured into water (200 ml) and extracted with diethyl ether (200 ml). The ether layer was washed with 10% acetic acid, followed by water then saturated NaCl and dried with $Na_2SO_4$. Evaporation of the ether gave a whitish foam (6.25 gm, 98%) which was the desired N-α-Fmoc L-glutamic acid N'-Boc-hydrazide-γ-t-butyl ester (8). $^1HNMR$ ($CDCl_3$, TMS) δ8.92 (br s, NH) 7.91–7.00 (m, 9H), 4.60–4.05 (m, 4H) 1.40 (s, 18H).

L-Glutamic acid-N'-Boc-hydrazide-γ-t butyl ester (9)

N-α-Fmoc L-Glutamic acid- N'-Boc-hydrazide-γ-t-butyl ester (0.70 gm, 1.3 mmole) was dissolved in 20 ml dry THF under nitrogen. Diethylamine (5 ml) was added and the reaction mixture stirred at room temperature for about 2 hours or until silica gel TLC ($CH_2Cl_2$:MeOH;9:1) indicated the disappearance of starting material($R_f$=0.45). After complete reaction, the mixture was evaporated and placed under vacuum to remove the last traces of amine. The crude product L-glutamic acid-N'-Boc-hydrazide -γ-t-butyl ester was used without further purification.

Methotrexate-α-N'-Boc-hydrazide γ-t-butyl-ester (10)

4-amino-4-deoxy-$N^{10}$- methyl pteroic acid 2,4-dinitrophenyl ester (6) (0.64 gm, 1.3 mmoles) prepared as described in Section 7.1.1.2 was dissolved in 30 ml of dry DMF and a solution of L-glutamic acid N'-Boc-hydrazide γ-t-butyl ester (0.41 gm, 1. 1.3 mmoles) in 5 ml of dry DMF was added, followed by addition of diisopropylethylamine (0.24 gm, 0.32 ml, 1.86 mmoles). The reaction mixture was stirred for 24–72 hours at room temperature. The reaction was monitored by TLC (silica gel $CH_2Cl_2$:MeOH:HOAc; 9:1:0.5) for the disappearance of the starting material and the formation of a new yellow spot ($R_f$=21) corresponding to the product. After complete reaction, the mixture was evaporated and flash chromatographed on silica gel using $CH_2Cl_2$:MeOH:HOAc; (9:1:0.5) to give methotrexate-α-N'-Boc hydrazide, γ-t-butyl ester as a yellow powder (0.60 gm, 74% yield.)

Methotrexate-α-hydrazide (7)

Methotrexate α-N'-Boc-hydrazide γ-t-butyl ester (0.60 was dissolved in 5 ml of $CH_2Cl_2$ and 5 ml of trifluoracetic acid was added and the reaction mixture stirred for 2 hours, evaporated and neutralized by addition of ammonium bicarbonate (0.025 M, 100 ml) and the solution purified on a QAE Sephadex® column using an ammonium bicarbonate gradient to yield 100 mg of methotrexate α-hydrazide as a yellow powder after lyophilization.

7.1.3. Methotrexate-α,α-Lysyl-Glycyl-Glycyl-Tyrosyl-Hydrazide (11)

Tyrosine N'-Boc-hydrazide (12)

A solution of CBZ-L-tyrosine (3.00 gm, 9.11 mmoles), N-methylmorpholine (0.92 gm, 1.00 ml, 9.11 mmoles) in 100 ml dry tetrahydrofuran (THF) was cooled to 0° C. under nitrogen. 2,2,2-Trichloro-1,1-dimethylethylchloroformate (2.18 gm, 9.11 mmoles) was added to the cold solution. After 5 minutes stirring, a solution of t-butyl carbazate (1.20 gm, 9.11 mmoles) in 20 ml dry THF was cooled to 0° C. and added to the reaction mixture. The mixture was allowed to warm slowly to room temperature and was stirred for about 18 hours. The solvent was removed by rotary evaporation and the residue was partitioned between chloroform and water and the layers separated. The organic layer was washed with saturated NaCl dried over $Na_2SO_4$, filtered, and solvent evaporated to yield the crude protected product. The CBZ-protected product, CBZ-tyrosine N'-Boc-hydrazide, was purified on silica gel via flash chromatography using a mixture of petroleum ether and ethyl acetate (1:1).

After chromatographic purification, the CBZ moiety was removed from the protected product as follows: CBZ-tyrosine N'-Boc-hydrazide was dissolved in a mixture of absolute ethanol (250 ml) and glacial acetic acid (2 ml) and hydrogenated for 1 hour in a Parr apparatus (3–4 atm) in the presence of 0.5 gm of 5% Pd on carbon. The catalyst was removed by filtration and the solvent was removed by rotary evaporation to yield the ninhydrin positive product tyrosine N'-Boc-hydrazide (12). $^1$HNMR (d$_6$, DMSO, TMS) δ7.13 (d, 2H) 6.78 (d, 2H) 3.75–2.70 (m, 3H) 1.55 (s, 9H).

Glycyl-glycyl-tyrosine N'-BOC-hydrazide (13)

A solution of CBZ-glycyl-glycine (0.17 gm, 0.68 mmoles) and diisopropylethylamine (0.118 ml, 0.68 mmoles) in 100 ml dry DMF was cooled to 0° C. Isobutylchloroformate (0.088 ml, 0.68 moles) was added. After 5 minutes of stirring, a solution of tyrosine N'-Boc-hydrazide (12) (0.200 gm, 0.68 m moles) in dry DMF at 0° C. was added. The mixture was allowed to warm to room temperature and stirred overnight. Solvents were removed by rotary evaporation. The residue was suspended in water and extracted with ethyl acetate. The ethyl acetate layer was washed with saturated NaCl, dried over Na$_2$SO$_4$, filtered and evaporated to yield 0.274 gm (74%) of the product CBZ-glycyl-glycyl-tyrosine N'-Boc-hydrazide. $^1$HNMR (d$_6$ DMSO, TMS) δ7.58 (s, 5H) 7.14 (d, 2H) 6.77 (d, 2H) 5.11 (s, 2H) 3.72 (m, 5H) 2.90 (m, 2H) 1.50 (M, 9H). The CBZ-protected product (0.824 gm) was dissolved into a mixture of absolute ethanol (200 ml) and glacial acetic acid (2 ml). The mixture was hydrogenated on a Parr apparatus for 1 hour (3–4 atm) in the presence of 5% Pd on carbon (0.5 gm). The catalyst was removed by filtration and the solvent was removed by rotary evaporation to yield 0.5 gm of crude glycyl-glycyl-tyrosine N'-BOC-hydrazide product (13) containing some acetic acid. $^1$HNMR (d$_6$ DMSO, TMS) δ7.30 (d, 2H) 6.90 (d, 2H) 3.80–3.20 (m, 5H) 3.90 (m, 2H) 2.00 (CH$_3$COOH) 1.5 (s, 9H).

CBZ-Glutamic acid-γ-t-Butyl Ester-Lysine-(ε-BOC) (14)

A mixture of CBZ-L-glutamic acid-γ-t-Butyl ester-1-hydroxysuccinimide ester (3.50 gm, 0.0081 moles), diisopropylethylamine (2.82 ml, 0.0162 mole) and ε-t-Boc-L-lysine (1.98 gm, 0.0081 moles) in dry DMF (35 ml) was stirred under N$_2$ overnight. The DMF was removed by rotary evaporation. The residue was taken up in CH$_2$Cl$_2$, washed four times with water, once with saturated NaCl and dried over Na$_2$SO$_4$. Filtration and evaporation of the solvent yielded 4.0 gm of (14) as a waxy solid.

Glutamyl-γ-t-butyl-Lysyl-(ε-BOC)-glycyl-glycyl-tyrosine N'-BOC-hydrazide (15)

A solution of (14) (1.17 gm, 2.07 mmoles) and N-methylmorpholine (0.23 ml, 2.07 mmoles) in dry DMF (100 ml) was cooled to 0° C. under N$_2$. Isobutylchloroformate (0.27 ml, 2.07 mmoles) was added and stirred for 5 minutes at 0° C. A solution of (13) (0.8465 gm, 2.07 mmoles) in dry DMF was added to the reaction mixture. The reaction was allowed to warm to room temperature. DMF was removed by rotary evaporation. The residue was extracted with ethyl acetate and water. The organic layer was dried over Na$_2$SO$_4$, filtered and evaporated to yield 1.1 gm (64.7%) of the CBZ derivative of (15). $^1$HNMR (d$_6$, DMSO, TMS) δ7.55 (s, 5H) 7.21 (d, 2H) 6.80 (d, 2H) 5.13 (s, 2H) 3.90–1.80 (m, 21H) 1.40 (br, s 27H). This material was hydrogenated in ethanol (200 ml) and 2 ml acetic acid in the presence of 0.5 gm 5% Pd on carbon for one hour to remove the CBZ moiety yielding the ninhydrin positive product (15). $^1$HNMR (d$_6$ DMSO, TMS) δ7.51(d, 2H) 6.80 (d, 2H) 1.50 (br s, 27H).

Methotrexate-α-α-lysyl-glycyl-glycyl-tyrosyl hydrazide (11)

A mixture of N,N-diisopropylethyl amine (0.032 ml, 0.18 mmoles), diethyl phosphorocyanidate (0.018 ml, 0.12 mmoles) and 4-amino-4-deoxy-N$^{10}$-methylpteroic acid (prepared by the method of Rosowsky, et al., 1985, J. Med. Chem. 28: 660) (0.34 gm, 0.12 mmoles) in dry DMF (40 ml) was stirred under N$_2$ overnight. A solution of (15) (1.0 gm, 0.12 mmoles) and N,N-diisopropylethylamine (0.021 ml, 0.12 mmoles) in dry DMF was added dropwise to the reaction mixture. The mixture was heated to 50° C. for about 2 hours. The DMF was removed by rotary evaporation and the residue was triturated with water, filtered and dried to yield 0.080 gm. The product was deprotected by removal of the t-butyl ester and Boc protecting group by stirring it in a mixture of methylene chloride (5 ml), anisole (3 ml) and trifluoroacetic acid (5 ml) for 2 hours. The solvents were removed by rotary evaporation, and the residue was triturated with ether then filtered to yield 0.030 gm of product (11).

7.1.4. Aminopterin-γ-Hydrazide (AM-γ-HY) (16)

N-4 ((2,4-Diamino-6-pteridinyl)methylamin)benzoyl-L-glutamic acid-5-hydrazide, commonly termed "aminopterin-γ-hydrazide", was synthesized as follows:

4-Amino-4-deoxy-N$^{10}$-formylpteroic acid 2,4-dinitrophenyl ester (17)

4-Amino-4-deoxy-N$^{10}$-formylpteroic acid was prepared by the method of Rosowsky et al., 1985, J. Med Chem. 28: 660.

A solution of 4-amino-4-deoxy-N$^{10}$-formylpteroic acid (0.5 gm, 1.5 mmoles) in 50 ml of dry DMF was stirred with 3-(3-dimethylaminopropyl)-1-ethyl carbodiimide hydrochloride (0.43 gm, 2.25 mmoles) and 2,4-dinitrophenol (0.41 gm, 225 moles) at 25° C. for 24 hours. The reaction mixture was concentrated, triturated with isopropanol, and filtered. The yellow solid was collected and dried in vacuo at 40° C. to yield 4-amino-4-deoxy-N$^{10}$-formylpteroic acid 2,4-dinitrophenyl ester (0.77 gm, 100%). R$_f$=0.31 (Merck silica gel, CH$_2$Cl$_2$:MeOH:HOAc; 9:1:0.5).

N$^{10}$-Formyl Aminopterin-αt-butyl ester γ-N'-Boc-hydrazide (18)

A mixture of 4-amino-4-deoxy-N$^{10}$-formylpteroic acid 2,4-dinitrophenyl ester (17) (1.00 gm, 2 mmoles) and L-glutamic acid α-t-butyl ester γ-N'-Boc-hydrazide (3) (0.70 gm, 2.2 mmoles) was stirred in 35 ml of dry DMF at 25° C. for 24 hours. After removal of DMF by rotary evaporation, the residue was taken up in CH$_2$Cl$_2$:MeOH:HOAc (9:1:0.5) and applied to a silica gel column which was eluted with the same solvent mixture. Fractions containing the product were pooled and evaporated to obtain (18) as a yellow solid, (1.05 gm, 82, R$_f$=0.21, blue fluorescent spot, (CH$_2$Cl$_2$:MeOH:HOAc, 9:1:0.5).

Aminopterin-γ-hydrazide (16)

Trifluoroacetic acid (5 ml) was added to a solution of (18) (100 mg, 0.16 mmoles) in 5 ml of CH$_2$Cl$_2$. The reaction was monitored by TLC (silica gel, CH$_2$Cl$_2$:MeOH:NH$_4$OH; 5:4:1) to confirm the disappearance of (18) (R$_f$=0.95) and the formation of a new blue fluorescent spot (R$_f$=0.62). After 40 minutes the reaction was complete and was rotary evaporated to dryness. The compound was then dissolved in 5 ml of 1 N NaOH and 10 ml of MeOH to remove the formyl group. The reaction was followed by TLC (silica gel, $CH_2Cl_2$:MeOH:$NH_4OH$;5:4:1) to observe the disappearance of the blue fluorescent color. When the blue fluorescent spot had disappeared, (about 2.5 hours), the reaction was complete and the mixture was neutralized to pH 7 with 0.5 N HCl. The reaction mixture was concentrated and lyophilized to obtain the crude yellow solid aminopterin-γ-hydrazide (16) Purification on QAE Sephadex ™ using an ammonium bicarbonate gradient (0.025 M to 0.5 M) and subsequent lyophilization yielded the pure aminopterin-γ-hydrazide (16) (0.03 gm, 40%).

7.1.5. Aminopterin-α-Hydrazide (19)

$N^{10}$Formyl-aminopterin-α-N'-BOC-hydrazide γ-t-butyl ester (20)

4-Amino-4-deoxy-$N^{10}$-formyl pteroic acid 2,4-dinitrophenyl ester (17) (0.50 gm, 1 mmole) prepared as described in Section 7.1.4. was dissolved in 50 ml dry DMF and L-glutamic acid N'-Boc-hydrazide-γ-t-butyl ester (9) (0.48 gm, 1.5 mmole) was added. The reaction mixture was stirred at room temperature for 72 hours and monitored by TLC (silica gel, $CH_2Cl_2$:MeOH:-HOAC;9:1:0.5) for appearance of a new yellow product ($R_f$=0.19). After complete reaction, the mixture was evaporated then flash chromatographed (silica gel, $CH_2Cl_2$:9:1:0.5) to give (20) (0.57 gm, 89%) as a single fluorescent spot on TLC.

Aminopterin-α-hydrazide (19)

$N^{10}$ Formyl-aminopterin α-N'-BOC-hydrazide γ-t-butyl ester (0.57 gm) was dissolved in $CH_2Cl_2$(20 ml) and trifluoracetic acid (10 ml) was added. The reaction mixture was stirred at room temperature for 2 hours then rotary evaporated. The resulting oil was dissolved in 10 ml of 1N NaOH and stirred for 2 hours at room temperature until the blue fluorescent starting material disappeared on TLC (silica gel, $CH_2Cl_2$:MeOH:N-$H_4OH$;5:4:1). The reaction mixture was then neutralized with 1N HCl and diluted to 100 ml with 0.025 M $NH_4HCO_3$ solution. Ion exchange chromatography on QAE Sephadex ® using an ammonium bicarbonate gradient(0.025 M to 0.50 M) and subsequent lyophylization gives aminopterin α-hydrazide (19).

7.1.6. Methotrexate-α-α-Lysine (21)

L-Glutamyl-γ-t-butyl ester-α-Lysine (ε-CBZ)-Diphenylmethyl Ester (22)

N-methylmorpholine (0.26 ml, 2.35 mmoles) was added to a solution of FMOC-glutamic acid-γ-t-butyl ester (1.00 gm, 2.35 mmoles) in dry DMF (10 ml) at 0° C. Isobutyl chloroformate (0.32 gm, 2.35 mmoles) was added and the reaction mixture stirred at 0° C. for 10 minutes. ε-CBZ-L-lysinediphenylmethyl ester (1.10 gm, 2.35 mmoles) was added after which the reaction mixture was allowed to warm to room poured into 300 ml water and extracted with ethyl acetate. After separation of the layers, and drying the organic layer with $Na_2SO_4$, the solvent was removed to give a solid. The solid product was taken up in THF (25 ml) and the FMOC moiety was removed using diethylamine (0.84 gm, 1.2 ml, 12.0 mmoles) at room temperature for 2 hours. The solution was evaporated to dryness to yield the oily product (22).

Methotrexate-α-α-lysine (21)

4-Amino-4-deoxy $N^{10}$-methylpteroic acid (0.76 gm, 2.35 mmoles) was added in small quantities to a solution of diiosopropylethylamine (1.23 ml, 7.05 mmoles) and diethylphosphorocyanidate (1.07 ml, 7.05 mmoles) in dry DMF (100 ml) with stirring. TLC of the reaction mixture after 1 hour showed the reaction was complete.

Compound (22) (1.52 gm, 2.35 mmoles) was added and the mixture incubated by stirring at room temperature overnight. The reaction mixture was evaporated to dryness. The oil that remained was dissolved in $CHCl_3$ and washed several times with cold, saturated $NaHCO_3$. The organic layer was dried with $Na_2SO_4$ and evaporated to dryness and the resulting solid was purified via silica gel flash chromatography using $CH_2Cl_2$:MeOH (95:5). The product was dissolved in 30 ml HBr in HOAc (30–32%) and stirred at room temperature for 4 hours. Analysis by HPLC indicated the cleavage was complete and that a single product had formed. Ether (100 ml) was added to the reaction mixture to precipitate the product. The mixture was centrifuged and the pellet was washed several times with ether. The pellet was then suspended in cold (0° C.) propylene oxide to neutralize the hydrobromide salt and then filtered. The yellow solid, methotrexate-α-α-lysine (21) eluted as a single peak by HPLC analysis on $C_{18}$ silica gel.

7.2. Preparation of Antibody Conjugates

7.2.1. MTX-γ-HY-Antibody

In one series of experiments MTX-Y-HY-antibody conjugates were prepared according to the present invention as follows:

A rat monoclonal IgG2c antibody, designated CTY015 specific for a Class I Major Histocompatability (MHC) antigen of Brown Norway (BN) rats (Smilek et al, 1980, J. Exp. Med. 151: 1139) was used. The monoclonal antibody was harvested either from ascites produced in nude mice or from the supernatant of an antibody-producing hybridoma cell line cultured in vitro. The antibody obtained was purified by gradient elution using a protein A-Sepharose column (Pharmacia Fine Chemicals, Piscataway, N.J.). The purity of the antibody preparation was confirmed by sodium dodecylsulfate (SDS) polyacrylamide gel electrophoresis.

The oligosaccharide moiety of the CYT015 antibody was oxidized by incubation, in the dark, with 10 mM $NaIO_4$ in phosphate buffered saline (PBS; 0.15 M NaCl, 0.01 M $PO_4$, pH 6.0) for one hour on ice. Excess $NaIO_4$ was then removed from the oxidized antibody using either dialysis or gel filtration techniques. The modified antibody (7 μm) was then incubated with MTX-γ-Hy at a concentration of 1 mM in the dark at room temperature overnight. Unreacted MTX-γ-Hy was removed by dialysis against PBS.

7.2.2 MTX-α-α-Lysine-ε-Antibody

In another series of experiments MTX-antibody conjugates were prepared in which the MTX analog was coupled to the aldehyde moiety of an oxidized antibody via a reactive primary amine moiety as follows:

MTX-α-α-lysine (having a free reactive ε-$NH_2$ group on the lysine moiety) was prepared as described in Section 6.1.4 above. The CYT015 antibody was oxidized as described in section 6.2.1 above. Oxidized antibody (1.0 mg/ml) was reacted with 1 mM MTX-α-α-lysine and 10 mM sodium cyanoborohydride (NaCNBH₃) overnight at room temperature in the dark. Excess NaCNBH₃ and unreacted MTX-α-α-lysine were removed by dialysis against PBS. Prior to use in vivo, this MTX-α-α-lysine-ε-antibody conjugate is preferably passed through a gel filtration column to remove any aggregates that may have been formed.

8. SUPERIOR THERAPEUTIC EFFECT OF SITE SELECTIVE ANTIBODY-MTX-γ-Hy

The following experiment demonstrates that the site selectively attached MTX-antibody conjugate of the present invention results in superior therapeutic effects in comparison to analogous randomly attached conjugate when administered in vivo.

An MTX-γ-Hy-antibody conjugate was prepared using CYT015 as described in Section 6.2.1. (referred to as "MTX-Hy-CYT015"). A randomly attached MTX-antibody conjugate was prepared using the same CYT015 antibody. Methotrexate (MTX) was non-selectively coupled to the lysine residues of the CYT015 antibody following the method of Kanellos et al., 1985, J. Nat'l Cancer Inst. 75: 319 (referred to as "Random MTX-CYT015"). Unreacted MTX was removed by dialysis against PBS.

The in vivo therapeutic effects of the conjugates were evaluated in female nude mice (NIH Swiss-Webster, Taconic Farms, N.Y.) injected subcutaneously in the left flank with $1 \times 10^6$ BN lymphoma cells. On the fourth day after injection, most animals had palpable tumors. Beginning on Day 4, and continuing through Day 8, animals were injected intraperitoneally with either of the antibody-conjugates, i.e., either MTX-CYT015 or Random MTX-CYT015. Because only about one-half the amount of drug could be randomly attached per antibody molecule (as compared to selective attachment), about one half the amount of site-selective conjugate was administered in order to compare equivalent doses of drugs. A group of untreated animals bearing BN tumor xenografts served as controls. Animals were weighed and tumor dimensions were measured daily. Results are illustrated in FIGS. 1 and 2.

As demonstrated in FIG. 1, the site selective MTX-Hy-CYT015 exerts a striking therapeutic effect on animals bearing tumor xenografts when compared to an identical group of animals which received no treatment. Animals receiving the site selective conjugates underwent tumor regression. In contrast, as demonstrated in FIG. 2 animals receiving an equivalent drug dose by way of randomly attached MTX-CYT015 conjugate showed only a slight therapeutic effect (compare e.g. MTX-CYT015 (7.5 μg MTX-Hy on 0.5 mg CYT015) vs. Random MTXCYT015 (7 0 μg MTX on 10 mg CYT015).

9. IN VITRO CLEAVAGE OF METHOTREXATE-α-α-LYSYL-GLYCL-GLYCYL-TYROSYL-HYDRAZIDE ANTIBODY CONJUGATE

The following experiment demonstrates that an antibody-peptide-MTX conjugate according to the Present invention can be enzymatically cleaved thus releasing free MTX in vitro. It is contemplated that cleavage would also take place in vivo at a tumor target site, catalyzed by enzymes such as plasmin and carboxypeptidase, thus releasing free therapeutically active MTX at the intended specific target site.

Methotrexate-α-α-lysyl-glycyl-glycyl-tyrosyl-hydrazide (11) (MTX-α-α-K-G-G-Y-NHNH₂) was prepared as described in Section 6.1.2 above. A CYT015 antibody conjugate was prepared by oxidizing the antibody as described in Section 6.2 and coupling the hydrazide moiety of the MTX-α-α-K—G—G—Y—NHNH₂ to the aldehyde moieties of the antibody.

The antibody=N N H—Y—G—G—K—MTX conjugate (1 mg/ml in pH 7.4 PBS) was reacted with trypsin (500 μgm/ml) for 3 hours at 37° C. Analysis of the digest by thin layer chromatography indicated release of MTX-α-α-Lysine from the conjugate. After inhibition of trypsin with diisopropylphosphoro fluoridate, carboxypeptidase B was added. Free MTX was released. Carboxypeptidase B alone did not cleave MTX or MTX-α-α-Lysine from the conjugate, confirming the obligatory two-step sequence of cleavages which would presumably occur in vivo catalyzed by enzymes such as plasmin and carboxypeptidase N. Carboxypeptidase N is found in blood, carboxypeptidase B is found only in the digestive tract. The carboxypeptidase B, however, serves as a good in vitro model for carboxypeptidase N because both enzymes have similar specificity.

What is claimed is:

1. A method for synthesis of an amine derivative of methotrexate or aminopterin, comprising:
   (a) reacting a free carboxyl of an N-protected L-glutamic acid having a free carboxyl group and a protected carboxyl group with a moiety containing a reactive amine or a protected reactive amine selected from the group consisting of primary amine, secondary amine, hydrazine, hydrazide, phenylhydrazine, alkoxyamine, semicarbazide and thiosemicarbazide to form an N-protected L-glutamic acid derivative containing a reactive amine or protected reactive amine;
   (b) removing the N-protecting group from the N-protected L-glutamic acid derivative formed in step (a) to form an L-glutamic acid derivative containing a reactive amine or protected reactive amine;
   (c) reacting the free α-amino group of the L-glutamic acid derivative formed in step (b) with an activated carboxyl group of either 4-amino-4-deoxy-N¹⁰-methyl pteroic acid or 4-amino-4-deoxy-N¹⁰-formyl pteroic acid, wherein said carboxyl group is activated by known carboxyl activating agents; and
   (d) removing any protecting groups to form a reactive amine-containing water-soluble derivative of either methotrexate or aminopterin wherein said derivative contains a reactive amine selected from the group consisting of primary amine, secondary amine, hydrazine, hydrazide, phenylhydrazine, alkoxyamine, semicarbazide and thiosemicarbazide.

2. The method according to claim 1, wherein the protected carboxyl group of the N-protected L-glutamic acid used in step (a) is the α-carboxyl group, and the free amino group of the L-glutamic acid derivative formed in step (b) is reacted with the activated carboxyl group of 4-amino-4-deoxy N¹⁰-methyl pteroic acid to form methotrexate-γ-hydrazide.

3. The method according to claim 1, wherein the protected carboxyl group of the N-protected L-glutamic acid used in step (a) is the γ-carboxyl group, and the free α-amino group of the L-glutamic acid derivative formed in step (b) is with the activated carboxyl group of 4-amino-4-deoxy $N^{10}$-methyl pteroic acid to form methotrexate-α-hydrazide.

4. The method according to claim 1, wherein the protected carboxyl group of the N-Protected L-glutamic acid used in step (a) is the α-carboxyl group, and the free α-amino group of the L-glutamic acid derivative formed in step (b) is reacted with the activated carboxyl group of 4-amino-4-deoxy $N^{10}$-formyl pteroic acid to form aminopterin-γ-hydrazide.

5. The method according to claim 1, wherein the protected carboxyl group of the N-protected L-glutamic acid used in step (a) is the γ-carboxyl group, and the free α-amino group of the L-glutamic acid derivative formed in step (b) is reacted with the activated carboxyl group of 4-amino-4-deoxy $N^{10}$-formyl pteroic acid to form aminopterin-α-hydrazide.

6. Aminopterin-γ-hydrazide.

7. Aminopterin-α-hydrazide.

8. Methotrexate-α-α-lysyl-glycyl-glycyl-tyrosyl hydrazide.

9. Methotrexate-α-hydrazide.

10. An amine-containing folic acid analog derivative selected from the group consisting of: methotrexate-α-hydrazide, 3',5'-dichloromethotrexate-α-hydrazide, methotrexate-α-α-lysyl-glycyl-glycyl-tyrosyl-hydrazide, methotrexate-γ-tyrosyl hydrazide, methotrexate-α-α-lysyl hydrazide, methotrexate-α-α-lysine, methotrexate-α-α-lysyl-ε-arginine-glycine-glycine-tyrosine, aminopterin-γ-hydrazide, aminopterin-α-hydrazide, 3'5'-dichloroaminopterin-γ-hydrazide, 3'5'-dichloroaminopterin-α-hydrazide, aminopterin-α-lysyl-glycyl-glycyl-tyrosyl-hydrazide, aminopterin-γ-tyrosyl-hydrazide, aminopterin-α-α-lysyl hydrazide, aminopterin-α-α-lysine, and aminopterin-α-α-lysyl-ε-arginine-glycine-glycine-tyrosine.

* * * * *